United States Patent [19]
Helmer et al.

[11] Patent Number: 5,638,284
[45] Date of Patent: Jun. 10, 1997

[54] METHOD OF QUANTIFYING THE WET STRENGTH OF PAPER

[75] Inventors: Ulla Helmer, Solna; Lars Renberg, Västerhaninge; Ralf Olsson, Stockholm, all of Sweden

[73] Assignee: Eka Nobel AB, Sweden

[21] Appl. No.: 444,052

[22] Filed: May 18, 1995

[30] Foreign Application Priority Data

May 18, 1994 [SE] Sweden ........................... 9401717

[51] Int. Cl.$^6$ ........................................... G06F 19/00
[52] U.S. Cl. ........................... 364/471.01; 162/263
[58] Field of Search ........................... 364/471, 150, 364/471.01, 525; 162/DIG. 10, 252, 253, 262, 263; 73/835

[56] References Cited

U.S. PATENT DOCUMENTS

| | | | |
|---|---|---|---|
| 5,104,485 | 4/1992 | Weyer. | |
| 5,121,337 | 6/1992 | Brown. | |
| 5,161,409 | 11/1992 | Hughes et al. | 73/153 |
| 5,206,701 | 4/1993 | Taylor et al.. | |
| 5,242,602 | 9/1993 | Richardson et al.. | |
| 5,243,546 | 9/1993 | Maggard | 364/571.02 |
| 5,276,327 | 1/1994 | Bossen et al. | 250/339 |
| 5,360,972 | 11/1994 | DiFoggio et al. | 250/339.12 |
| 5,489,980 | 2/1996 | Anthony | 356/308 |
| 5,504,332 | 4/1996 | Richmond et al. | 250/339.12 |

OTHER PUBLICATIONS

S.D. Brown, "Chemometrics", Anal. Chem. 62, pp. 84R–101R (1990).
Pulp characterization using spectroscopy and multi-variate data analysis, L. Wallbäcks, Dept. of Organic Chemistry, Univ. of Umeå, Sweden (1991).
Research Disclosure, Method of Measurement of Chemicals in Paper, Dec. 1992/945 Abstract of Research Disclosure 344066 by Hercules Incorporated.

*Primary Examiner*—Paul P. Gordon
*Assistant Examiner*—Robert J. Dolan
*Attorney, Agent, or Firm*—Burns, Doane, Swecker & Mathis, LLP

[57] ABSTRACT

A method for the quantification of the wet strength of paper in pulp and/or paper, comprising (I) developing a calibration model by
  (I.a) registering absorption, reflectance or emission spectra of reference samples of known wet strength to develop learning sets;
  (I.b) processing the spectral raw data, to reduce noise and adjust for drift and diffuse light scatter;
  (I.c) performing a data analysis by applying chemometric techniques to the processed learning sets; and (II) determining the unknown paper wet strength by registering the absorption, reflectance or emission spectra, in correspondence to (I.a), from the pulp and/or paper of the unknown wet strength; processing the thereby obtained spectral raw data as according to (I.b); and applying the developed calibration model to the processed data.

Optionally, a data analysis step as according to (I.c) can also be applied to the processed spectral raw data from the paper having unknown wet strength.

19 Claims, 2 Drawing Sheets

METHOD OF QUANTIFYING THE WET STRENGTH OF PAPER

FIELD OF THE INVENTION

The present invention is directed to a method of quantifying the physical parameter wet strength of pulp and paper, and more particularly to a method for the analysis of wet strength in pulp and paper.

BACKGROUND OF THE INVENTION

For a number of paper applications the physical parameter of wet strength is of fundamental importance, examples being that of papers of tissue quality, as well as in e.g. paper-bags and paper-sacks.

The Technical Association of Pulp and Paper Industries (TAPPI) defines the wet strength of a paper as the tensile strength of the paper after it has been completely soaked with water. An untreated paper keeps only 2-8% of its original dry strength when soaked with water. However, the wet strength of a paper can be improved by the addition of wet strength enhancing additives to the pulp, making it possible to retain as much as 25-40% of the dry tensile strength in the wet paper.

Paper obtains its strength from the interfibrillar hydrogen bonds which are created when the cellulose fibres are drawn together by surface tension during the drying process. When the paper is re-wetted, the fibres swell and the hydrogen bonds are loosened up and destroyed. The paper looses its strength. Wet strength agents help to retain some of the strength, up to 40-45% of the dry strength, when the paper is fully soaked in water.

The true mechanism behind wet strength is not yet fully understood and there is a possibility that different agents may give wet strength by different mechanisms.

Chemicals giving wet strength are all water-soluble synthetic polymers, prepolymers, with functional groups. They have the possibility to react further, to crosslink and increase the molecular weight during the drying process. They are all added to the stock as solutions in water or as colloids (mainly melamine resins). They are cationic by charge and are retained by their charge and molecular weight mainly on the fines particles. The anionic charge is much stronger and the surface area is many times larger of those fines than of the coarse fibres.

Three main mechanisms can be postulated for the wet strength:

The first postulate suggests that resin and fines particles containing a lot of resin are accumulated at the fibre-fibre crossing by the forces produced during the drying process. The resin crosslinks with itself, homo crosslinking, in the mixture. A composite material of resin and cellulose is formed. Those covering layers, on both sides of the fibre, protect against water and the fibres are kept in place and cannot swell. The hydrogen bonding between the fibres are more or less undisturbed and the strength is retained.

The second postulate suggests that when the paper treated with wet strength resin, is heated the resin is cured. The crosslinked polymer forms a net work on the surface of the coarse fibres which protects the existing fibre to fibre bond, making them resistant to water. This protection maintains the strength of the paper by reducing the swelling in the bonding areas.

The third postulate suggests that there is a reaction between the resin and the cellulose fibres. Such chemical bonding would result in the cellulose fibres having a reduced swelling capacity in water which would lead to less breaking of the interfibrillar bonds.

Wet strength resins were developed rather late in the history of paper making. It was not until the 1940s that different urea-formaldehyde (and melamine formaldehyde) formulations were tested as wet strength agents and they remained being commercially important wet strength resins since then. Improvements have been made and other polymers have been developed during the years.

Urea-formaldehyde, UF, resins are low in cost, they are easy to repulp and are not sensitive to interference with dissolved substances in the paper making system. Two stages are involved when making urea-formaldehyde resins.

The first stage is the methylolisation of urea by formaldehyde in a molar ratio of slightly above two formaldehyde to one urea. Some cationic amines are added to the mixture where they react with formaldehyde and are incorporated in the resin via methylol groups.

The second stage involves condensation polymerisation between the methylol end groups, promoted by high temperature and low pH's, resulting in ether or methylene linkages, with the elimination of a water molecule or a formaldehyde molecule.

The polymerisation process is interrupted at a certain molecular weight by lowering the temperature and changing the pH above 7. The resins are delivered to the paper mill as solutions with dry contents around 40% and with the ability to crosslink further. Urea-formaldehyde resins do not need pre-treatment at the paper mills. A pH of 4,5 in the white water system is the optimum for the use of urea-formaldehyde. It is also a well known fact that urea formaldehyde resins need both time and temperature to crosslink, cure, totally. That is why only half of the possible final wet strength usually is achieved off machine. Full wet strength is then reach after two or three weeks depending on how the paper reels are stored. The resins can be added as delivered at almost any point in the system. Typically resin addition levels vary between 0,5 to 3,0 % depending on the type of paper products desired.

The mechanism behind the efficiency of urea formaldehyde resin is either the first or the second postulate defined at p. 2 or both.

The resin has been fully investigated and the methylol groups are not able to react with hydroxyl groups on fibres and fines. The crosslinking occurs only within the resin itself, homo crosslinking. The awareness of environmental problems has led to new urea formaldehyde resins with low emission of formaldehyde.

Both urea and melamine resins require acid conditions to cure effectively in the paper. Alkaline-curing amine epichlorohydrin condensation products, PAAE, related to epoxy resin adhesives, were invented in the 1950s. They gained immediate acceptance and started to replace urea formaldehyde in many formulations where pH could be increased. They offered high cost-effectiveness, compatibility with alkaline sizes, reduced machine corrosion, and other benefits.

The most common polymeric amine-epichlorohydrine resin is prepared in two steps. At first the polymer backbone is produced from a dibasic acid such as adipic acid which is heated together with diethylenetriamine forming a linear polyamineamide by condensation. The second step involves a reaction between epichlorohydrin and all the secondary amine groups in the backbone. The chlorohydrine groups formed by the epichlorohydrin are transformed to reactive azetidiniumgroups which react with the tertiary amino groups in the backbone forming a rather crosslinked, still water soluble, net work. This crosslinking is interrupted at a certain molecular weight by lowering the temperature and changing the pH below 5. The resin is delivered to the paper mill as a solution with a dry content around 20% and with the ability to crosslink further. The resin is added to the stock and retained mainly by the fines.

The cured resin is not easy to hydrolyse. Therefore the wet strength imparted by azetidinium-type resins is permanent rather than fugitive and proper attention to special techniques is required for successful broke reworking. The awareness of environmental problems has led to new PAAE resins with very low content of chlorinated byproducts, which could give contribution to AOX (Adsorbable Organic Halogenates).

The UF and PAAE resins are dominating the market for wet strength but there are some other polymers used mainly for specific paper products. Glyoxylated polyacrylamide (gPAM) is specifically used in wet strength towelling. gPAM is prepared by crosslinking of a low molecular weight PAM with glyoxal. The PAM is normally prepared with a cationic co-monomer of a quaternary type to provide good retention to the fibres or fines. gPAM is supposed to impart wet strength to paper primarily through covalent bond formation between resin and fibre. The bonding is formed by reaction between a hydroxyl group from the cellulose and an aldehyde group from the resin. These bonds are formed where gPAM is adsorbed onto the fibre surfaces within the fibre-to-fibre bonded area. Drying conditions are said to favour formation of an extensive amount of covalent bonding between the resin net work and each of at least two contacting fibres.

The method of measuring the wet strength presently used in the paper production industry is also defined by TAPPI. According to this method, the wet strength, in terms of e.g. the wet tensile index, in kNm/kg, is mechanically measured in the standard test method T 456 m-49 using a standardized instrument, a tensile tester. Briefly, this quite straightforward method consists of soaking a paper sample in water and measuring the tensile strength of the thus treated paper in the tensile tester.

When testing the wet strength of a paper in a paper production plant, the paper sample is taken at the end of the paper machine, from the last roll, called the reeling drum. Only when the reeling drum is full, containing a large quantity of paper, e.g. 20 tonnes the sampling is performed.

Before testing the wet strength, the paper sample must be submitted to an accelerated curing. This curing step is necessary in order to obtain a relevant measure of the wet strength of the paper since the paper on the roll is also naturally subject to a certain curing, whereby the wet strength is somewhat increased.

One major drawback with this way of monitoring the wet strength is the delay between a change in a parameter at the manufacturing of a paper and the answer of the determination of the wet strength of that paper. This delay may lead to important losses in case the wet strength proves to be inadequate since, by the time this assessment has been accomplished, there may be very large quantities of paper of this inadequate wet strength produced.

It is obvious that the method of testing the wet strength presently in use in the paper production industry is a drawback to the productivity and the economy of the paper production process. Thus, there is a definite need for a more convenient method of testing the wet strength in the paper manufacturing industry.

The present invention has for an object to offer a solution to said problem, by providing a method that allows the monitoring of the wet strength of the paper during the production process. This object is attained by the combined use of spectrometric and chemometric techniques.

According to the invention, the paper or the pulp in or from the production line is submitted to spectrometric analysis. However, the pulp as well as the paper represents a multi-component system or a system having a high degree of background interferences which increases the problems of spectrometric analysis.

The use of multivariate data analysis in the characterization of multi-component systems is presently a field of development. Applied generally to the field of chemistry, and particularly to the field of analytical chemistry, those several statistical methods also are termed chemometric methods, forming the discipline of chemometrics. The technique of chemometrics is more fully explained in S. D. Brown, "Chemometrics", Anal. Chem. 62, 84R-101R (1990), which by reference is incorporated herein in its entirety.

An example of the use of chemometrics is given in the thesis of Wallbäcks (Pulp characterization using spectroscopy and multivariate data analysis, L. Wallbäcks, Dept. of Organic Chemistry, Univ. of Umeå, Sweden (1991)), who has shown that multivariate data analysis can be used to predict various physical properties as a function of the initial characteristics of the unbeaten pulp and the effect of beating.

Further, Brown et al, in the U.S. Pat. No. 5,121,337 (1990) disclose a method, based on multivariate data analysis, for correcting spectral data for data due to the spectral measurement process itself and estimating unknown property and/or composition data of a sample using such method.

On the other hand, Richardson et al, in U.S. Pat. No. 5,242,602 disclose a method for simultaneously measuring the concentration of multiple chemical components, which they call performance indicators, in an aqueous system, by the analysis of the spectrum of the aqueous system in the wavelength range 200 to 2500 nm and by applying chemometric algorithms to the spectrum to simultaneously determine the concentrations of the different performance indicators.

Weyer, U.S. Pat. No. 5,104,485 discloses a method for measuring extremely low concentrations of non-aqueous constituents or chemicals in a water/matrix, including differentiating between pulp fines and extremely low concentrations of individual chemicals in a water/cellulose matrix such as occur in papermaking. The water/matrix is exposed to the near-infrared spectrum from 1000 to 2500 nm to produce a record voltage that is directly proportional to the absorption by the non-aqueous constituent. The amount non-aqueous constituent is determined from voltage values of incremental additions of the non-aqueous constituent.

In addition Hercules reported in a research disclosure (December 1992/945) that in the papermaking process, a water/cellulose mixture is laid on a wire screen and the water is filtered off leaving the fibers and various additives. The paper sheet produced is composed of cellulose fibers, fillers such as clay and calcium carbonate, and additives such as optical brighteners, sizes, and wet and dry strength resins. Various instrumental systems are available for measuring some of these constituents such as the clay. These systems, however, are limited in the determinations that can be carried out. A method for determining several individual chemical constituents simultaneously in a paper sheet has been developed according to Hercules. Radiation from a near infrared sourse is allowed to impinge upon the paper sheet, and after interaction of the radiation with the chemical constituents in the sheet, the reflected radiation is collected and stored. The chemical composition is calculated from the stored data after mathematical treatments are applied. The measurement system is calibrated via samples of known composition. Use of the full near infrared spectrum from 1100 to 2500 nanometers permits the analysis of several constituents simultaneously, especially when derivatives are employed as part of the mathematical treatment. This analysis aids in determining the extent of retention of the chemical additives and fillers.

However, the present inventors have shown that four steps should be involved for a useful quantification of a chemical on the basis of spectroscopy. The first step is recording the determination of the emission, transmittance or reflectance values from a huge number of wavelengths (e.g. 300 to 600 numbers of wavelength are not uncommon). The second step is data processing the spectral data, which is essential in the NIR region (800–2400 nm). The third step is transformation of data, usually by centring, normalisation or autoscaling the data. The forth step is to find the mathematical expression for the calibration function (data analysis).

The description of the method according to Hercules only disclose the first and second step. The spectral information is collected, followed by an undefined mathematical treatment. The only detail that is given is the application of derivatives (which is a commonly used technique within spectroscopy). Nothing is revealed about the numerical algorithm used for the transformation of data and algorithm for calibration. These steps are of utmost importance to obtain a useful quantification of a chemical or a property on the basis of spectroscopy.

However, according to this invention specific algorithms have been applied to overcome especially two disadvantages, namely:

1. The number of wavelengths can be considerable and outnumbers the number of samples, used for the calibration. As an example, if the reflectance of 300 wavelengths are recorded for 20 samples, with conventional mathematical models only the values from the number of samples minus 2 can be used for the calibration. Thus, in this case only values from 20–2=18 wavelengths can be used and the information from the other 282 wavelengths cannot be taken into account. According to this invention all spectral information can be used and compiled by transferring all the information recorded into so called latent variables based on principal component analysis.

2. The spectral information is often highly correlated which seriously affect the success for quantification. If the spectral information is transferred into latent variables by principal component analysis a higher degree of orthogonalisation is obtained which can be a crucial factor for success.

Moreover, none of the above mentioned authors suggests how to solve the problem of determining the wet strength present in a paper in a paper production process in a way permitting the monitoring of these parameters and furthermore no details of the calibration procedures are given. It should be emphasised that the expression "determination" in this context can be interpreted either as a qualitative analysis or as a quantitative analysis. A qualitative analysis is the determination of the presence of a chemical or property while quantitativ analysis relates to the estimation of a certain value, including the degree of uncertainty of this value (expressed in statistical terms such as confidence interval etc.). The object of the present invention is to provide a reliable and precise way of monitoring—i.e quantification—the wet strength present in a paper by spectroscopic measurement in combination with multivariate data analysis using chemometrical techniques.

None of the above mentioned authors suggests how to solve the problem of determining the wet strength of a paper in a paper production process in a way permitting the monitoring of this parameter. This, however, is the object of the present invention, which provides a reliable and precise way of monitoring the wet strength of a paper by a rapid chemical analysis coupled with multivariate data analysis using the technique of chemometrics.

The object of the invention thus is to provide a method of determination of wet strength of paper in pulp and paper in real time without the use of the traditional lengthy mechanical measurements.

It is another object of the invention to provide a method of maintaining an effective process control programme wherein the wet strength of a paper is monitored to detect any change and provide control input, assuring optimum dosage levels for wet strength enhancing chemical additives and mechanical treatment of the pulp.

The methods and means as disclosed according to the invention are those as further defined in the claims.

SUMMARY OF THE INVENTION

The above objects of the invention are obtained by a method of measurement of the wet strength of paper by analysing the visible, near-infrared and/or infrared spectrum of the paper/pulp in the process line in a wavelength range within 400 nm to 400 µm, and applying chemometric evaluation of the spectrum to calculate the wet strength of the paper.

DETAILED DESCRIPTION OF THE INVENTION

Figure 1:
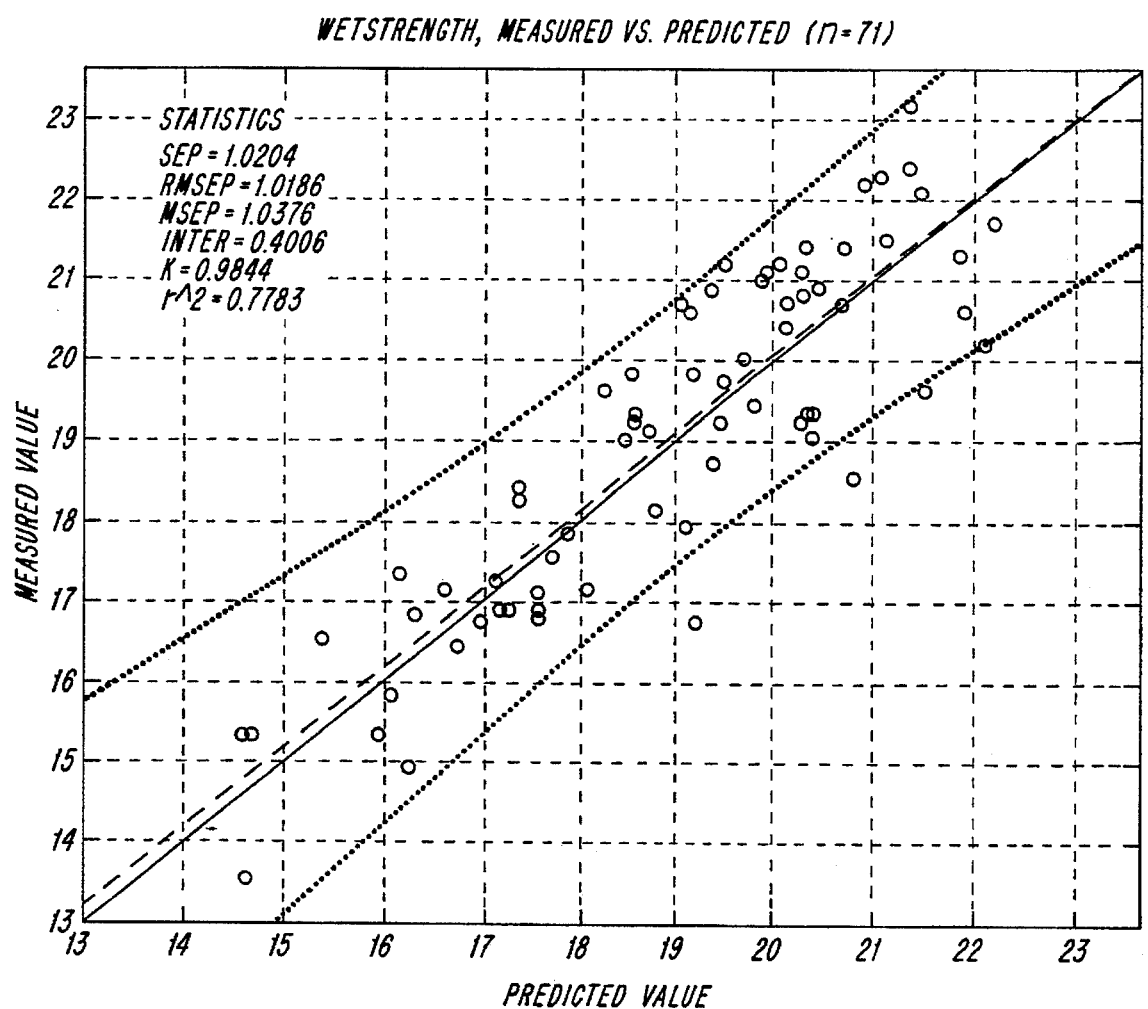

According to the invention it has now, by an extensive development work, been shown that it is possible to record the absorption, reflectance and emission spectra of pulp and paper using an UV-VIS-NIR and/or IR spectrometer and, by the use of absorbance, reflectance or transmittance values at discrete wavelengths from these spectra, calculate the wet strength of the corresponding paper.

The terminology pulp and/or paper as used herein refers not only to bleached pulp and/or paper, but also to unbleached or partially bleached pulp and/or paper. This includes sack paper, liner and the like as well as creped paper qualities.

Technically, the spectrometric analysis can be carried out as a monitoring process, by use of an on-line, in-line or at-line probe, or by taking individual samples for separate analysis (off-line). In both cases, the emission, transmittance or reflectance spectra are subject to further data treatment using values from several discrete wavelengths from each particular spectrum.

An example of such a technique is the use of a device, placed at a distance from the process, containing a light source, detector, electronic components and other necessary components to transmit a signal through an optical fibre to the sample, where the light is transmitted through or reflected on or partly through the sample. The resulting signals are returned to the detector in an accompanying optical fibre cable, and recorded.

In the spectrometer, the light is converted into an electric signal which is then conveyed to a computer where the spectrum of a previously stored reference scan can be related to, e.g. subtracted from, the sample spectrum and a reference corrected spectrum is calculated.

Another example is by manually or automatically taking samples at relevant time intervals and submitting the samples to analysis in an analytical instrument, containing the light source, detector, electronic components and other necessary components. The emission, transmittance or reflectance spectra are then subjected to further data treatment, using values from several discrete wavelengths from each particular spectrum.

The detection is performed in the UV-VIS-NIR wavelength range of 200 nm to 2500 nm, preferably 800 nm to 2500 nm, and/or the IR wavelength range of 2500 nm to 400 µm. This can be accomplished by the use of a scanning instrument, a diode array instrument, a Fourier transform instrument or any other similar equipment, known to the man skilled in the art.

It is preferred that the detector have a measuring interval of at the most 10 nm, preferably 2 nm, and most preferably 1 nm or less.

An evaluation of wavelengths which contain absorption, reflectance or emission provides features relevant for the analysis. By way of the application of chemometrical methods to the obtained spectra it is then possible to ignore wavelengths which do not contain information that contribute to the chemical analysis, even though the measurement will include information from the entire wavelength range.

The determination and control of the wet strength of paper in pulp and/or paper by use of the spectrometric measurements comprise three main stages, the first main stage being the development of a calibration model, involving the development of learning sets; data processing; and data analysis, by use of pulp and/or paper samples of known wet strength; and the second main stage being that of the spectrometric analysis of the sample of the unknown wet strength, spectral data processing, optionally followed by data analysis; and application of the calibration model, developed in the first main stage, to the thereby obtained data.

(I) DEVELOPMENT OF A CALIBRATION MODEL

The wet strength is measured in the traditional way (e.g. according to TAPPI) for a number of pulp and/or paper samples. These samples, characterized by traditionally measured wet strength values, then are used in the development of a calibration model wherein the three stages mentioned above are applied to the registered absorption, reflectance or emission spectra of said samples.

(I.a) Development of Learning Sets

Model learning sets consist of a large number of absorption, reflectance or emission spectra from the samples with known wet strength characteristics, which samples preferably should be representative of the production line. The learning sets are used in the chemometric algorithms to calculate the resulting model parameters.

(I.b) Data Processing

To reduce noise and adjust for base line drift the spectral raw data should be processed. This processing may also reveal hidden information, such as identity of apparently dissimilar spectra or non-identity of apparently very similar spectra.

Moreover, the assumptions leading to Beer's law (stating that, for a given absorption coefficient and length of the optical path in the absorptive media, the total amount of light absorbed is proportional to the molecular concentration of the sample) are usually not fulfilled in the complex system that constitutes the pulp or paper. This is mostly due to light scatter variation depending on the physical dimensions of the sample.

Various theories have been developed to overcome this problem and the most used are:

1) The Kubelka-Munk transform (P. Kubelka, F. Munk, Z. Tech. Physik 12, 593 (1931)), which takes account of absorption and scatter, is according to Eq. 1:

$$A_{ik} = \frac{(1 - R_{ik})^2}{2R_{ik}} \tag{1}$$

where $R_{ik}$ is the apparent absorbance at the wavelength k, $A_{ik}$ is the transformed absorbance at the wavelength k, and the index i represents the sample spectra available.

2) The Multiplicative Scatter Correction (MSC) (P. Geladi, D. MacDougall, H. Martens, Appl. Spect. 39, 491–500 (1985)) where each spectrum is 'corrected' in both offset and slope by comparing it to an 'ideal' spectrum (the mean spectrum), is according to Eq. 2:

$$A_{ik} = \frac{R_{ik} - \hat{a}_i}{\hat{b}_i} \tag{2}$$

where $A_{ik}$, $R_{ik}$, i and k have the same meanings as above, $\hat{a}_i$ is the least squares estimation of the intercept parameter, and $\hat{b}_i$ is the least squares estimation of the slope parameter.

3) The use of derivatives, e.g. up to the fourth order derivatives (A. Savitzky, M. J. E. Golay, Anal. Chem. 36, 1627–1639 (1964)). The derivative of the spectrum results in a transformed spectrum, consisting only of the relative changes between the adjacent wavelengths, and it has been shown that the peak intensities of derived spectra tend to be more linear with concentration (T. C. O'Haver, T. Begley, Anal. Chem. 53, 1876 (1981)).

4) The use of the Fourier transformation, or by use of the Standard Normal Variate transformation as disclosed in R. J. Barnes, M. S. Dhanoa and S. J. Lister, Appl. Spectrosc., Vol. 43, number 5, pp. 772–777 (1989).

(I.c) Data Analysis

Data analysis using chemometric techniques then allows the calibration model to be developed. There are several chemometric techniques which can be used, such as Principal Component Analysis (PCA), Partial Least Squares Regression (PLS), Principal Components Regression (PCR), Multilinear Regression Analysis (MLR) and Discriminant Analysis. The preferred chemometric technique according to the invention is the PLS method.

(I.c.1) Principal Component Analysis (PCA)

By PCA, a set of correlated variables is compressed into a smaller set of uncorrelated variables.

This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models.

In general, 2 to 15 principal components will account for 85% to 98% of the variance of the variables.

(I.c.2) Partial Least Squares Regression (PLS)

PLS is a modelling and computational method by which quantitative relations can be established between blocks of variables, e.g. a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is detailedly disclosed in Carlsson R., Design and optimization in organic synthesis, B. G. M. Vandeginste, O. M. Kvalheim, Eds., Data handling in science and technology (Elsevier, 1992), vol. 8.

(I.c.3) Principal Components Regression (PCR)

PCR is closely related to PCA and PLS. As in PLS, each object in the descriptor block is projected onto a lower dimensional space yielding in scores and loadings. The scores are then regressed against the response block in a least squares procedure leading to a regression model which can be used to predict unknown samples. The same model statistics as in PLS and PCA can be used to validate the model.

For an exellent tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

(I.c.4) Multilinear Regression Analysis (MLR)

By MLR, the best fitting plane for the wet strength as a function of the spectra is defined, using least squares techniques to define each boundary of the plane. This plane then is used to recognize and assign a predicted value to an unknown wet strength.

This technique is generally limited to relatively 'clean' systems where there is not a significant amount of matrix interference and, in contrast to PLS, it requires more objects than variables.

(I.c.5) Discriminant Analysis

This is a method whereby, by use of spectral data, the known wet strength values are grouped into different clusters, separated by linear decision boundaries.

From its spectrum, a sample of unknown wet strength then can be matched to a cluster, and the wet strength can be assigned a value, e.g. the average value of the cluster.

This is a very useful technique for quality screening, but requires a very large data base to obtain statistically significant results.

(II) DETERMINATION OF THE UNKNOWN WET STRENGTH BY APPLICATION OF THE CALIBRATION MODEL

Once a calibration model has been developed, the determination of the unknown paper wet strength can be performed by registering the absorption, reflectance or emission spectrum, in correspondence to (I.a), from the pulp and/or paper of the unknown wet strength; processing the thereby obtained spectral raw data as according to (I.b); optionally performing a data analysis on the processed spectral data as according to (I.c); and applying the developed calibration model to the thereby obtained data.

The invention will now be illustrated by way of examples.

EXAMPLE

Diffuse reflectance near-infrared spectrometry (NIRR) of the paper sample, linearisation of spectral data and multivariate data evaluation using the PLS-algorithm were used to determine the wet strength of the paper.

DEVELOPMENT OF A CALIBRATION MODEL (A) Development of Learning Sets

SAMPLES

The reference samples consisted of in total 108 paper sheets of different paper qualities of bleached and unbleached pulp, 37 of bleached pulp and 71 of unbleached pulp, the latter being of both creped and uncreped qualities:

samples made in a Laboratory Dynamic Sheet Former, from hardwood 35° SR, grammage 70 g/m$^2$;

samples made on a pilot paper machine, from bleached craft pulp (50/50 softwood-hardwood) 35°–39° SR, grammage 70 g/m$^2$;

samples of both ordinary and creped (crepe grade 3%) qualities from unbleached craft pulp with 30–40% recycled fibres, 20°–25° SR, varying porosity 14.1–17.4 Gurley sec, grammage 70 g/m$^2$, density 600 kg/m$^3$ samples from different paper mills, such as liner of hardwood, grammage 160–180 g/m$^2$.

The paper samples had been subjected to treatment with different amounts of wet strength increasing paper additives. The wet strength of the samples was tested, using the standard TAPPI method mentioned herein above.

Paper samples containing UF-resin were produced at an experimental paper machine with the following experimental parameters:

| | |
|---|---|
| Pulp: | unbleached hardwood, sulphate, 32° SR |
| Chemicals: | UF-resin, added amount 0 to 3% dry weight on dry fibre and alum 1,5 %, pH = 4,5 (H$^2$SO$_4$.), resulting in 51 samples |
| Temperature: | 20° C. |
| Grammage: | 70 g/m$^2$ |
| Machine: | system closed. |
| Press sect.: | 1) 4 bar, 2) 1 bar |
| Drying section: | 60/80/95/110° C. |

The 51 samples were tested for wet strength and scanned by NIRR and a model was developed (results see Table I):

TABLE I

| DESCRIPTOR | R+e,cir +ee 2 | SEP | MSEP | RMSEP | #PC:S | RSDb(%) | RSDW (%) |
|---|---|---|---|---|---|---|---|
| Wet breaking length om. | 0.948 | 114.0 | 12780 | 113.0 | 9(6) | 6.40(4.91) | 2.62(1.58) |
| Wet breaking length 600* om. | 0.934 | 134.7 | 17810 | 133.4 | 9(6) | 1.90(7.70) | 10.16(2.61) |
| Wet breaking length c. | 0.952 | 194.9 | 37250 | 193.0 | 9(6) | 6.01(6.05) | 6.08(10.98) |
| Wet strength om. | 0.957 | 1.107 | 1.203 | 1.097 | 10 | 6.30(5.46) | 2.26(8.59) |
| Wet strength c. | 0.962 | 1.774 | 3.094 | 1.759 | 10 | 5.78(7.77) | 3.32(11.58) |

*all the samples were related to the same density

NEAR INFRARED REFLECTANCE (NIRR) MEASUREMENTS

The NIRR measurements were obtained using a NIR Systems® 6500 spectrometer, from NIR systems, U.S., equipped with a High fat/moisture cell with a scan surface of up to 60 cm², with a spectral operating range between 400 nm and 2500 nm, in even intervals of 2 nm, yielding 1050 measurements at different wavelengths. Diffuse reflectance data were obtained as apparent absorbance, and transferred to a Macintosh® Quadra 700 computer.

(B) Data Processing

The spectral data matrix was reduced to the NIR region (1100–2500 nm) for greater modelling speed. The spectra were reduced by a factor of 8 (every eighth wavelength was kept), which resulted in 175 spectral points for modelling.

LINEARISING TRANSFORMATION

The best linearising function was established using a factorial design approach (R. J. O. Olsson, in Near Infra-Red Spectroscopy, I. T. Hildum, K. L. Naes T. and Tandberg A., Eds. Ellis Horwood Limited, Chichester, (1992) pp.103–107) and was found to be the MSC with mean spectrum subtraction and incorporating the calculated intercept and slope parameters in the independent dataset (spectra).

The Mean Squared Error Prediction (MSEP) (H. Martens, T. Naes, Appl. Spect. 39, 491–500 (1985)) according to Eq. 3 herein below was evaluated as a number of latent variables kept in the PLS model. The linearising function/functions that yielded the smallest MSEP for the different descriptors then was used in the subsequent PLS modelling.

$$MSEP = \frac{1}{n} \sum_{i=1}^{n} (\hat{c}_i - c_i)^2 \qquad (3)$$

n is the number of samples, $\hat{c}_i$ is the modelled descriptor value and $c_i$ is the traditionally measured descriptor value. The index i is the descriptor of the sample i.

(Other statistical parameters related to MSEP are the Standard Error Prediction (SEP) and the Root Mean Squared Error Prediction (RMSEP), given herein below by Eqs. 4 and 5, respectively.)

(C) Data Analysis

The MATLAB software V 3.5 was used for numerical calculations. The PLS-algorithm used for modelling the relationships between the spectra and descriptors is a customised function in the commercially available 'Chemometrics Toolbox' based on the NIPALS algorithm (H.Wold, P. Krishnaiah, Multivariate Analysis, 391 (1966)). The convergence criteria for the algorithm were $1 \times 10^{-10}$ or 100 iterations. The method of establishing the significant number of PLS-components was crossvalidation (S. Wold, Technometrics 20, 397–405 (1978)) (Jack-knifing) with one sample left out. This number here was found to be 15 for both the bleached and the unbleached paper samples. The wet strength values were mean-centered and scaled to unit variance prior to modelling (autoscaling or z-transform) and rescaled prior to model evaluation.

RESULTS

Figure 2:
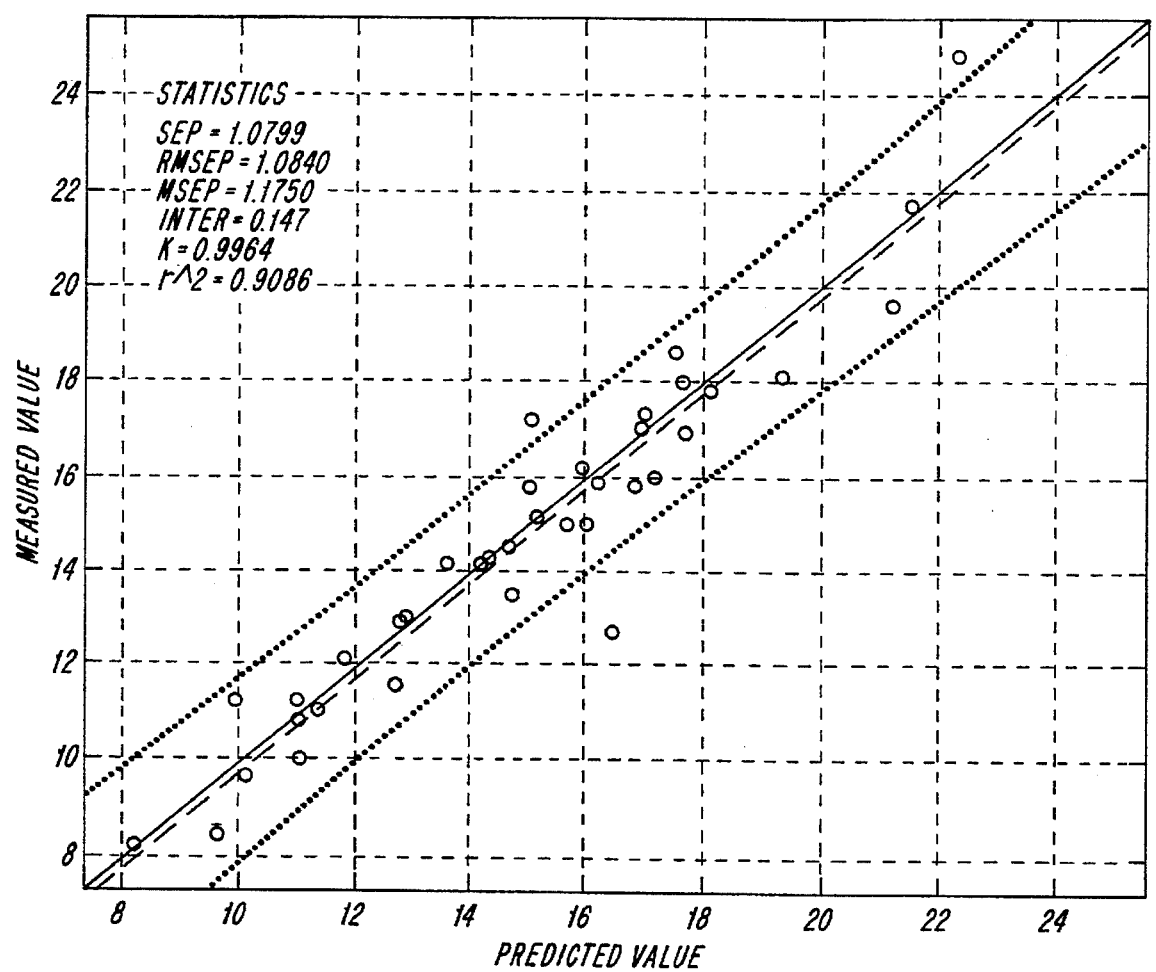

The measured vs. modelled values of the wet strength of unbleached (creped and uncreped), and bleached (uncreped) paper qualities are plotted in FIGS. 1 and 2, respectively, with a 95% t-test confidence interval for the, to the data, least squares fitted line.

Accordingly, FIG. 1 represents the measured vs. predicted wet strength (in kNm/kg) of 71 samples of unbleached paper, both creped and uncreped; and FIG. 2 represents the measured vs. predicted wet strength (in kNm/kg) of 37 samples of bleached, uncreped paper.

In the above mentioned figures are also specified the unadjusted correlation coefficient ($r^2$), SEP (in kNm/kg) (Eq. 4, herein below), RMSEP (in kNm/kg) (Eq. 5, herein below), MSEP (in kN²m²/kg²), the intercept (INTER) and the slope (K) of the curves.

$$SEP = \sqrt{(n-1)^{-1} \sum_{i=1}^{n} (\hat{c}_i - c_i - \overline{(\hat{c} - c)})^2} \qquad (4)$$

$$RMSEP = \sqrt{MSEP} \qquad (5)$$

(In Eq. 4, n, $\hat{c}$, c, and i respectively have the same meaning as in Eq. 3).

SEP is a good approximation of one standard deviation of the model residue.

Ideally, $r^2$ and k should be as close to 1 as possible; while SEP, RMSEP, MSEP, and the intercept should be as close to 0 as possible. In view of the values obtained, it will be possible to realize the very good validity and preciseness of the model.

Definitions of the statistical terms as used are given below.

| Symbols | |
|---|---|
| $y_i$ | Scalar y value for the i t:h sample i.e. the true reference analytical results. |
| $\hat{y}_2$ | The estimated $y_i$ value given by the PLS modelling. |
| $\bar{y}$ | Mean of $y_i$ values. |
| N | The total number of samples used for modelling. |

$r^2$ Correlation coefficient $$r^2 = \left( \frac{\sum_{i=1}^{N} (\hat{y}_i - \bar{y})^2}{\sum_{i=1}^{N} (y_i - \bar{y})^2} \right)$$

$r^2$ determines how well the data are adjusted to the least squares fitted straight line. Thus $r^2=1.00$ indicates that the calibration equation models 100% of the variation within the set of data. If $r^2=0.00$. then there is no correlation.

SEP Standard Error of Prediction $$SEP = \sqrt{\frac{\sum_{i=1}^{N} (\hat{y}_i - y_i - \overline{(\hat{y} - y)})^2}{(N-1)}}$$

SEP is a characterisation of the variance attributable to random unexplainable error.

MSEP Mean Square Error of Prediction $$MSEP = \frac{\sum_{i=1}^{N} (y_i - \hat{y}_i)^2}{N}$$

MSEP is the average squared differences between actual and predicted values. i.e. for a set of objects not present in the calibration. In the literature MSEP is also referred to as PRESS (Predicted Residual Error Sum of Squares)

RMSEP Root Mean Square Error of Prediction.

$$RMSEP = \sqrt{MSEP}$$

Transforms the MSEP into the original measured unit.

The advantage of the novel method of monitoring the wet strength of paper in pulp and paper using chemometrics thus should be readily apparent. Indeed, a wide variety of samples, originating from various paper mills and production processes, may be analysed using the same calibration set. The only criterion which must be considered is whether the sample is bleached or not. The invention thus provides a method whereby the monitoring of the wet strength of the paper in a paper production process can be performed in a very rapid and precise way on any type of pulp and paper.

We claim:

1. A method for the quantification of the wet strength of paper by analyzing absorption, reflectance or emission spectrum of the corresponding pulp or paper, which method comprises:
   (I) developing a calibration model by
      (I.a) registering absorption, reflectance or emission spectral raw data of reference samples of pulp or paper of known wet strength to develop a learning set;
      (I.b) processing the spectral raw data to reduce noise and adjust for drift and diffuse light scatter;
      (I.c) performing a data analysis by applying chemometric techniques to the processed learning set; and
   (II) registering absorption, reflectance or emission spectral raw data of a sample of pulp or paper of unknown wet strength; processing the spectral raw data as according to step (I.b); and applying the developed calibration model on the processed spectral data in order to determine the unknown wet strength.

2. A method according to the claim 1, wherein the recording of the absorption, reflectance or emission spectra is performed in the wavelength range of 200 nm to 400 µm.

3. A method according to claim 2, wherein the recording of the absorption, reflectance or emission spectra is performed in the wavelength range of 800 nm to 2500 nm.

4. A method according to the claim 1, wherein the spectral data processing in step (I.b) is preformed using the Kubelka-Munk transform:

$$A_{ik} = \frac{(1-R_{ik})^2}{2R_{ik}} \quad (1)$$

wherein $R_{ik}$ is the apparent absorbance at the wavelength k, $A_{ik}$ is the transformed absorbance at the wavelength k, and the index i represents the sample spectra available.

5. A method according to the claim 1, wherein the spectral data processing in step (I.b) is performed using the Multiplicative Scatter Correction:

$$A_{ik} = \frac{R_{ik} - \hat{a}_i}{\hat{b}} \quad (2)$$

wherein $R_{ik}$ is the apparent absorbance at the wavelength k, $A_{ik}$ is the transformed absorbance at the wavelength k, $\hat{a}_i$ is the least squares estimation of the intercept parameter, and $\hat{b}$ is the least squares estimation of the slope parameter, the index i representing the sample spectra available, and the index k representing the available wavelengths.

6. A method according to the claim 1, wherein the spectral data processing in step (I.b) is performed by use of the Fourier transformation.

7. A method according to the claim 1, wherein the spectral data processing in step (I.b) is performed by use of up to the fourth order derivatives.

8. A method according to the claim 1, wherein the spectral data processing in step (I.b) is performed by use of the Standard Normal Variate transformation.

9. A method of quality screening the wet strength of a paper using the method according to claim 1, wherein the data analysis is performed by use of the Discriminant Analysis.

10. A method according to claim 1, wherein the data analysis is performed by use of the Multilinear Regression Analysis technique.

11. A method according to claim 1, wherein the data analysis is performed by use of the Principal Component Analysis technique.

12. A method according to claim 1, wherein the data analysis is performed by use of the Principal Components Regression technique.

13. A method according to claim 1, wherein the data analysis is performed by use of the Partial Least Squares technique.

14. A method for maintaining a process control program wherein the wet strength of a paper is monitored to detect any change thereof and provide control input in order to assure optimum dosage levels for wet strength enhancing chemical additives and mechanical treatment of the pulp, by the use of a method as defined in claim 1.

15. A method according to claim 1, wherein a data analysis on the processed spectral data obtained from the pulp and/or paper of the unknown wet strength is performed by the use of the Multilinear Regression Analysis technique.

16. A method according to claim 1, wherein a data analysis on the processed spectral data obtained from the pulp and/or paper of the unknown wet strength is performed by the use of the Principal Component Analysis technique.

17. A method according to claim 1, wherein a data analysis on the processed spectral data obtained from the pulp and/or paper of the unknown wet strength is performed by the use of the Principal Components Regression technique.

18. A method according to claim 1, wherein a data analysis on the processed spectral data obtained from the pulp and/or paper of the unknown wet strength is performed by the use of the Partial Least Squares technique.

19. A method according to claim 1, wherein in step (I.c) the processed spectral data of the reference samples are transferred into latent variables based on Principal Component Analysis, and chemometric techniques are applied on the latent variables in order to find the mathematical expression of the calibration model; and in that in step (II) the processed spectral data are transferred into latent variables as according to step (I.c), and the developed calibration model is applied on the latent variables in order to determine the unknown wet strength.

* * * * *